(12) United States Patent
Usher et al.

(10) Patent No.: US 7,513,890 B2
(45) Date of Patent: Apr. 7, 2009

(54) FLUID MANIFOLD CONTROL DEVICE

(75) Inventors: Kathryn Mary Usher, Gansevoort, NY (US); Colin Hart, Queensbury, NY (US); Thomas Deyette, Jr., Hudson Falls, NY (US)

(73) Assignee: Navilyst Medical, Inc., Marlborough, MA (US)

( * ) Notice: Subject to any disclaimer, the term of this patent is extended or adjusted under 35 U.S.C. 154(b) by 557 days.

(21) Appl. No.: 10/430,716

(22) Filed: May 6, 2003

(65) Prior Publication Data
US 2004/0221904 A1 Nov. 11, 2004

(51) Int. Cl.
*A61M 5/00* (2006.01)
*F16K 11/074* (2006.01)
(52) U.S. Cl. .............................. 604/248; 167/625.46
(58) Field of Classification Search ................ 604/247, 604/248, 537, 534, 284, 32, 99.04; 137/625.46, 137/6, 625.47
See application file for complete search history.

(56) References Cited

U.S. PATENT DOCUMENTS

| | | | |
|---|---|---|---|
| 3,157,201 A * | 11/1964 | Littmann | 137/625.47 |
| 4,084,606 A | 4/1978 | Mittleman | |
| 4,540,027 A | 9/1985 | Forberg | |
| 4,838,269 A | 6/1989 | Robinson et al. | |
| 4,892,524 A | 1/1990 | Smith | |
| 5,057,120 A | 10/1991 | Farcot | |
| 5,074,334 A | 12/1991 | Onodera | |
| 5,104,387 A * | 4/1992 | Pokorney et al. | 604/248 |
| 5,127,904 A | 7/1992 | Loo et al. | |
| 5,129,887 A | 7/1992 | Euteneuer et al. | |
| 5,135,026 A | 8/1992 | Manska | |
| 5,190,067 A | 3/1993 | Paradis et al. | |
| 5,232,024 A * | 8/1993 | Williams | 137/883 |
| 5,238,026 A | 8/1993 | Goto | |
| 5,334,170 A | 8/1994 | Moroski | |
| 5,356,375 A | 10/1994 | Higley | |
| 5,423,751 A | 6/1995 | Harrison et al. | |
| 5,431,185 A | 7/1995 | Shannon et al. | |
| 5,490,837 A | 2/1996 | Blaeser et al. | |
| 5,536,247 A | 7/1996 | Thornton | |

(Continued)

FOREIGN PATENT DOCUMENTS

EP 1 090 650 A1 4/2001

(Continued)

OTHER PUBLICATIONS

International Search Report for PCT/US2004/004612 dated Feb. 17, 2004.

(Continued)

*Primary Examiner*—Kevin C Sirmons
*Assistant Examiner*—Catherine N Witczak
(74) *Attorney, Agent, or Firm*—Orrick Herrington & Sutcliffe, LLP (57) ABSTRACT

A manifold is disclosed which includes a manifold body that defines a main lumen, a primary injection line and a port. A check valve system is also provided which permits flow from the primary injection line to the main lumen while selectively preventing back flow from the main lumen to the primary injection line and, simultaneously, permitting flow from the port to the primary injection line while preventing back flow from the primary injection line to the port.

3 Claims, 9 Drawing Sheets

U.S. PATENT DOCUMENTS

| | | | |
|---|---|---|---|
| 5,562,614 A | 10/1996 | O'Donnell | |
| 5,569,208 A | 10/1996 | Woelpper et al. | |
| 5,573,515 A | 11/1996 | Wilson et al. | |
| 5,575,767 A | 11/1996 | Stevens | |
| 5,586,579 A * | 12/1996 | Diehl | 137/614.17 |
| 5,593,385 A | 1/1997 | Harrison et al. | |
| 5,618,268 A | 4/1997 | Raines et al. | |
| 5,665,074 A | 9/1997 | Kelly | |
| 5,743,872 A | 4/1998 | Kelly | |
| 5,779,666 A | 7/1998 | Teirstein | |
| 5,833,706 A | 11/1998 | St. Germain et al. | |
| 5,843,051 A | 12/1998 | Adams et al. | |
| 6,083,205 A | 7/2000 | Bourne et al. | |
| 6,099,511 A | 8/2000 | Devos et al. | |
| 6,315,762 B1 | 11/2001 | Recinella et al. | |
| 6,371,942 B1 | 4/2002 | Schwartz et al. | |
| 6,520,937 B2 | 2/2003 | Hart et al. | |
| RE38,074 E | 4/2003 | Recinella et al. | |
| 7,172,572 B2 * | 2/2007 | Diamond et al. | 604/32 |
| 2002/0038105 A1 | 3/2002 | Schwartz et al. | |

FOREIGN PATENT DOCUMENTS

GB  2 274 148 A  7/1994

OTHER PUBLICATIONS

Written Opinion of the International Searching Authority for PCT/US2004/004612 dated Feb. 17, 2004.
Partial International Search Report dated Sep. 7, 2004.

* cited by examiner

FLUID MANIFOLD CONTROL DEVICE

FIELD OF THE INVENTION

The present invention relates generally to devices used for injecting agents during intravascular medical procedures.

BACKGROUND OF THE INVENTION

During angiography and angioplasty procedures, fluid manifolds also known as "fluids administration sets" are employed which are connected to a catheter and which enable the physician to administer saline, contrast solution and other agents and fluids to the patient.

Typical manifolds include a distal end that is connected to the catheter and a proximal end that is connected to an injection syringe or pump. The injection syringe or pump, is typically used to inject saline or a contrast agent solution into the catheter. The manifold typically includes a plurality of ports connected to the manifold through a stop cock connection. The ports are used to inject contrast solutions and other medicaments into the catheter and may also provide a connection to a pressure transducer or other analytical equipment. Further, the opening and closing of these ports typically requires the physician to rotate a stop cock handle or other manually operated valve.

Accordingly, there is a need for an improved manifold system for use with angiographic procedures which minimizes the need for manual operation of valves relating to the injection of saline and contrast fluid.

SUMMARY OF THE DISCLOSURE

A manifold control device is disclosed which can be used in catheterization and other procedures and which results in a simplified aspiration and injection of agents without the need for a manual valve operation by the physician.

An improved manifold is disclosed which comprises a main lumen having proximal and distal ends in a primary injection line connected to the proximal end of the main lumen. A port is connected to the main lumen between the proximal and distal ends thereof. A check valve is provided which permits flow between the primary injection line to the main lumen while selectively preventing back flow from the main lumen to the primary injection line. The check valve also permits flow from the port to the primary injection line while preventing back flow from the primary injection line to the port.

A method for administering fluid is also disclosed which comprises injecting fluid through a primary injection line to a main lumen while selectively preventing back flow from the main lumen to the primary injection line and injecting fluid through a port to the primary injection line while preventing back flow from the primary injection line and main lumen to the port.

DETAILED DESCRIPTION OF THE PRESENTLY PREFERRED EMBODIMENTS

Figure 1:
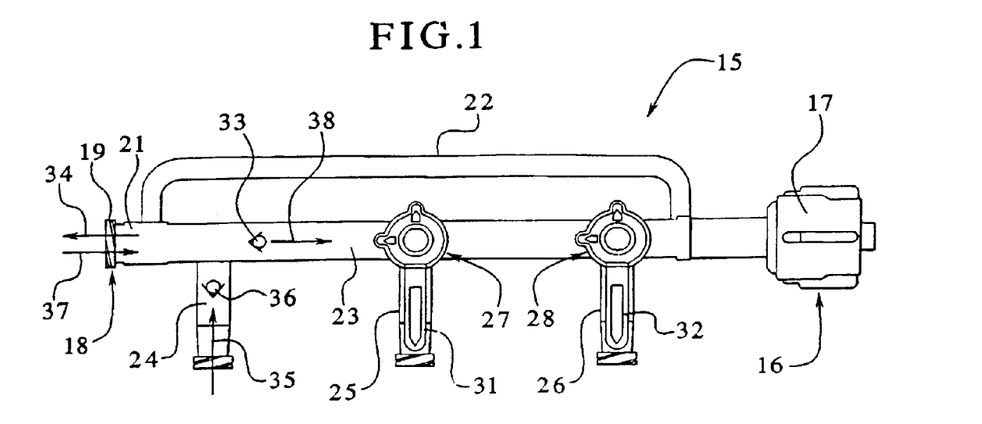
FIG. 1 is a schematic plan view of an angiographic fluid manifold made in accordance with the present invention.

FIG. 1 illustrates a manifold 15 which includes a distal end 16 with a male connection 17 that can be connected to a catheter (not shown). The system 15 also includes a proximal end 18 with a female connection 19 that may be connected to a syringe (not shown). The proximal end 18 and syringe (not shown) define a primary injection line 21. The system 15 further includes a manifold body 22 which has a main lumen 23 extending therethrough. In addition to the primary injection line 21, the main lumen 23 is connected to a port 24 and additional secondary ports 25, 26. Ports 24, 25, 26 are integrally connected to corresponding fluid lines (not shown). While the structure of the invention may be utilized for systems other than manifolds, it is anticipated that a primary use for the present invention may be utilized as a fluid manifold, and more particularly, for an angiographic fluid manifold. Accordingly, the port 24 will typically be connected to a contrast fluid or solution reservoir (not shown) via corresponding fluid lines (not shown). The additional ports 25, 26 may be connected to a pressure transducer or other analytical device (not shown) or may serve as a waste or fluid collector (not shown). The ports may be opened and closed with the stop cocks shown at 27, 28. The stop cocks 27, 28 are easily manipulated by way of the handles 31, 32.

In operation, a syringe connected to the female connector 19 of the primary injection line 21 can be used to inject saline or other fluid through the main lumen 23 to the catheter (not shown) The check valve 33 permits flow from the primary injection line 21, through the main lumen 23 to the catheter (not shown). The check valve 33 also prevents back flow from the main lumen 23 towards the primary injection line and syringe (not shown). Thus, the saline supply or other fluid at the syringe (or other pumping means such as, for example, an electric or manual pump) will not be contaminated by fluid disposed downstream in the main lumen 23 or catheter (not shown).

To inject fluid, e.g., contrast fluid from the port 24 to the main lumen, the syringe or other pump (not shown) is aspirated by creating a pressure drop in the direction of the arrow 34 As fluid flow in this direction from the main lumen 23 is prevented by the check valve 33, fluid flows from the port 24 in the direction of the arrow 35 and though the primary injection line 21. The fluid flows past the check valve 36 Fluid from the port, e.g., which may be retained in the syringe or pump connected to the primary injection line, may be injected into the main lumen by generating pressure at the syringe or pump and creating a pressure drop in the direction of the arrow 37 thereby causing the fluid that originated in the port 24 to flow past the cheek valve 33 in the direction of the arrow 38, into the main lumen and thereafter into the catheter (not shown). The check valve 36 prevents back flow fern the syringe or pump (not shown) connected to the primary injection line 21 from flowing past the check valve 36, into the port 24 and thereby contaminating the supply or reservoir or fluid connected to the port 24.

Thus, both the supply of saline or other fluid retained in the syringe or pump connected to the port 24 and the fluid, such as contrast fluid retained in the reservoir connected to the port 24 may be protected from contamination, The fluid retained in the reservoir connected to the port 24 may be protected from contamination both by fluid retained in the syringe or pump connected to the primary injection line 21 as well as fluid disposed in the main lumen 23 downstream of the cheek valve 33. Any fluid retained in the syringe or pump connected to the primary injection line 21 may be protected from contamination by any fluid disposed in the main lumen downstream of the check valve 33.

Figure 2:
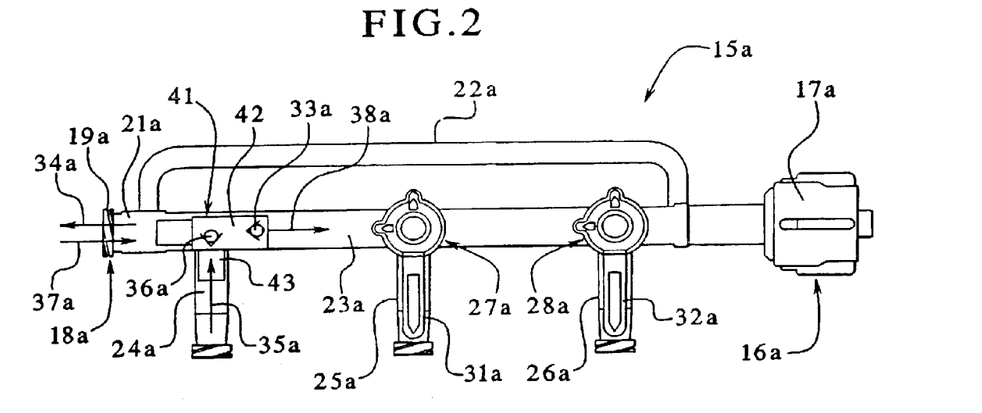
FIG. 2 is another schematic plan view of an angiographic fluid manifold made in accordance with the present invention.

Using like reference numerals to refer to like or similar parts but with the suffix "a" an alternative embodiment system 15a is shown in FIG. 2. Instead of the check valve 36a being disposed in the port 24a, the two check valves 33a, 36a are disposed within a body 41. The body 41 includes a first lumen 42 and a second lumen 43. The first lumen 42 is disposed at least partially in the main lumen 23a and, in the embodiment shown in FIG. 2, accommodates both check valves 33a and 36a. The first and second lumens 42, 43 are connected to form a t-connection. As an alternative, the check valve 36a may be disposed in the second lumen 43 which is at least partially disposed within the port 24a.

Figure 3:
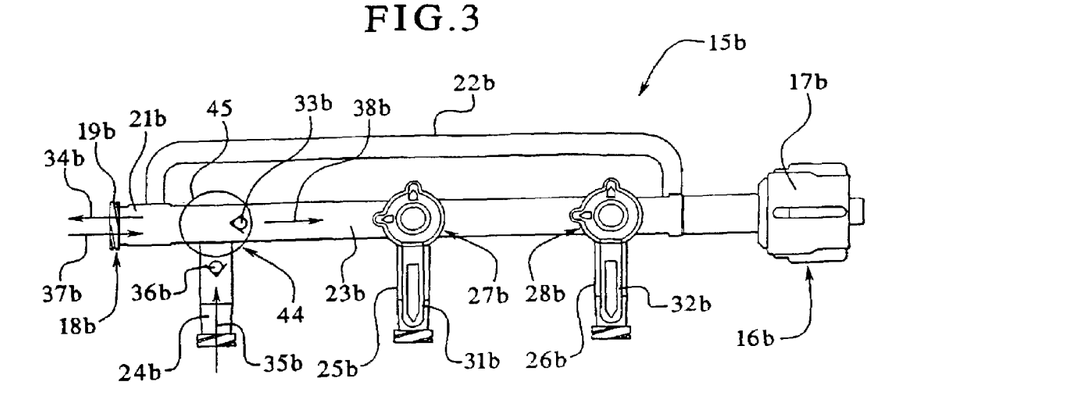
FIG. 3 is yet another schematic plan view of an angiographic fluid manifold made in accordance with the present invention.

Again using like reference numerals for like or similar parts except for the suffix "b," the check valve 33b of FIG. 3 is connected to a push button mechanism 44 which includes a movable body 45 which is connected to the check valve 33b as well as the body 22b which defines the main lumen 23b. Movement of the movable body 45 causes the check valve 33b to be disposed either in the main lumen 23b or be removed from the main lumen 23b.

Figure 4:
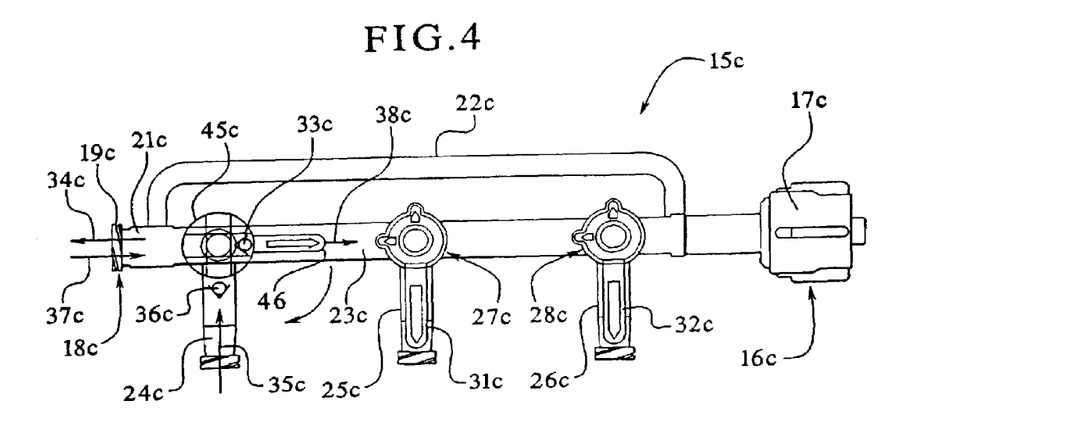
FIG. 4 is yet another schematic plan view of an angiographic fluid manifold made in accordance with the present invention.

In a further embodiment illustrated in FIG. 4, a movable body 45c as shown in FIG. 4 is rotatably connected to the manifold body 22c The check valve 33c is disposed in the rotatable body 45c and can be moved from an activated position as shown in FIG. 4, where the handle 46 is disposed parallel to the main lumen 23c, to the deactivated position shown in phantom in FIG. 4, where the check valve 33c is removed from the main lumen 23c In the embodiment 15c shown in FIG. 4, the cheek valve 36c is disposed in the port 24c.

Figure 5:
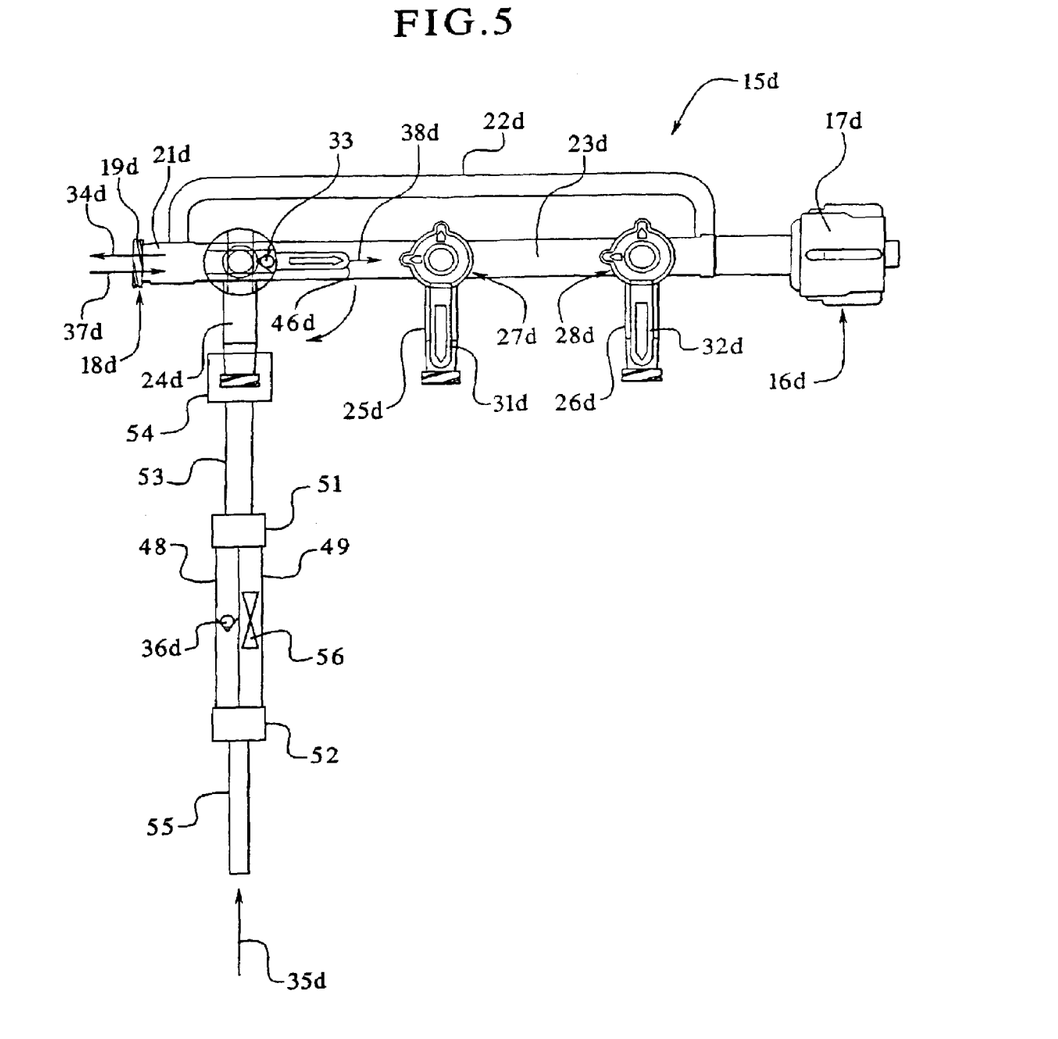
FIG. 5 is yet another schematic plan view of an angiographic fluid manifold made in accordance with the present invention.

In contrast, in the embodiment 15d shown in FIG. 5, the check valve 36d is disposed within a check valve line 48 that, along with a mechanical valve line are disposed between tube splitters 51, 52. The tube splitters 51, 52 are connected to the port 24d by way of the tubing 53 and male connector 54. The tubing 55 is connected to a fluid reservoir, such as, for example, a contrast fluid reservoir (not shown). The mechanical valve line 49 accommodates a manually operable mechanical valve 56. The check valve line 48 and mechanical valve line 49 may be rotated so as to permit one of the lines 48, 49 to be in communication with the tubings 53, 55 at a time.

The embodiment 15d shown in FIG. 5 is particularly useful if the syringe or pump connected to the primary injection line 21d has excess fluid in it or an air bubble. For example, excess contrast fluid may be injected from the primary injection line 21d back through the port 24d by rotating the lines 48, 49 so that the mechanical valve line 49 is in communication with the tubings 53, 55 and the valve 56 is opened. Thus, excess contrast fluid can be saved instead of wasted.

Figure 6A:
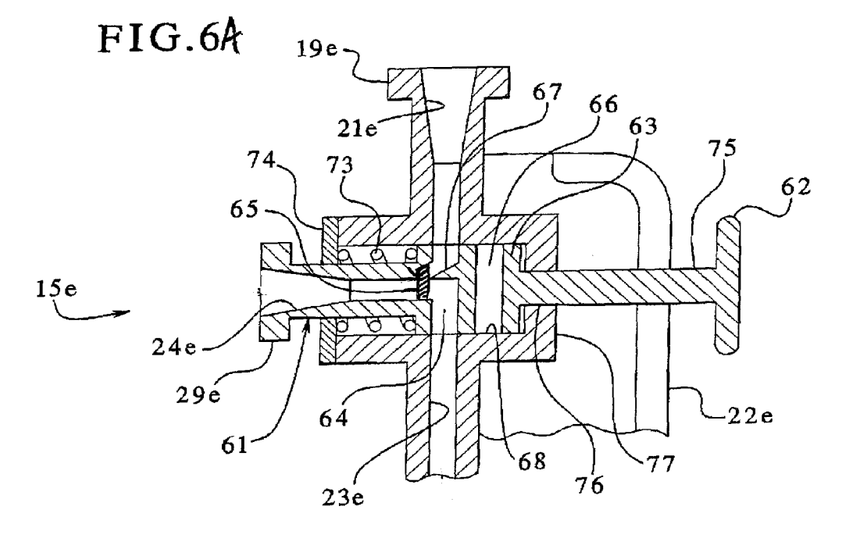
FIG. 6A is a partial sectional view of an angiographic fluid manifold made in accordance with the present invention in a first position and at a rest condition where the syringe, contrast port and primary injection line are isolated.
Figure 6B:
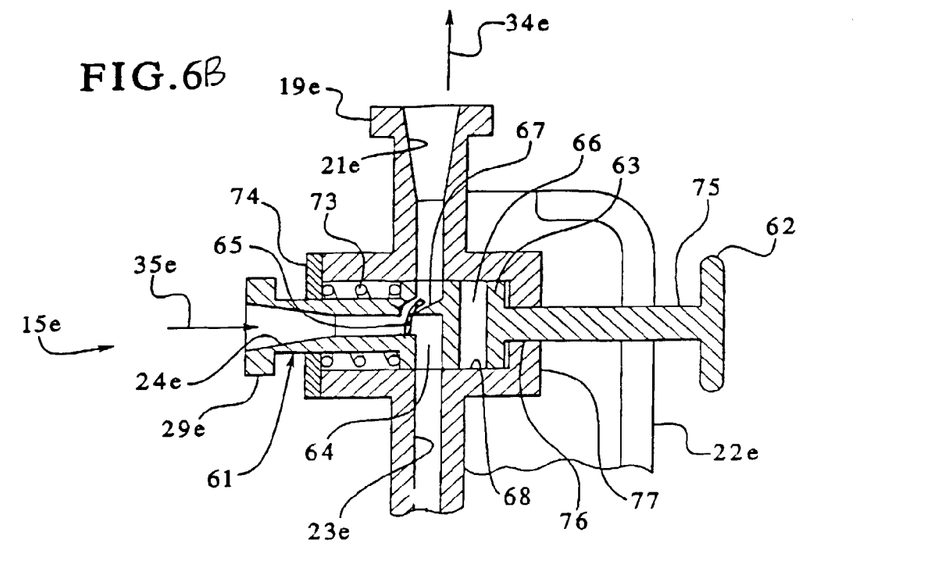
FIG. 6B is another partial sectional view of the angiographic fluid manifold shown in FIG. 6A, also in the first position but at a point in time where the syringe is being filled with contrast causing the valve to be flexed to permit flow between the contrast port and the syringe during aspiration of the syringe.
Figure 6C:
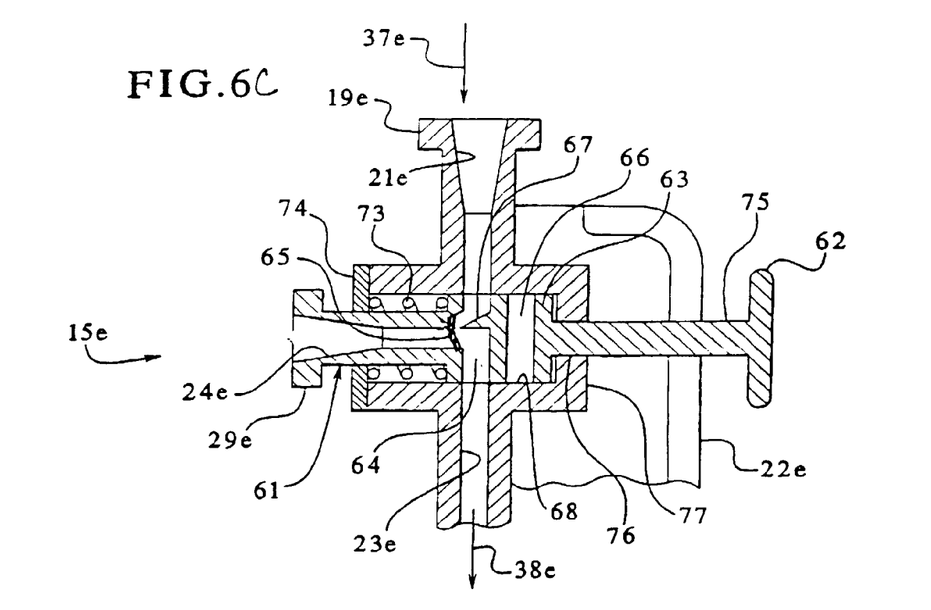
FIG. 6C is another partial sectional view of the angiographic fluid manifold shown in FIGS. 6A and 6B where contrast is being injected from the syringe to the primary injection line thereby isolating the contrast port.
Figure 7:
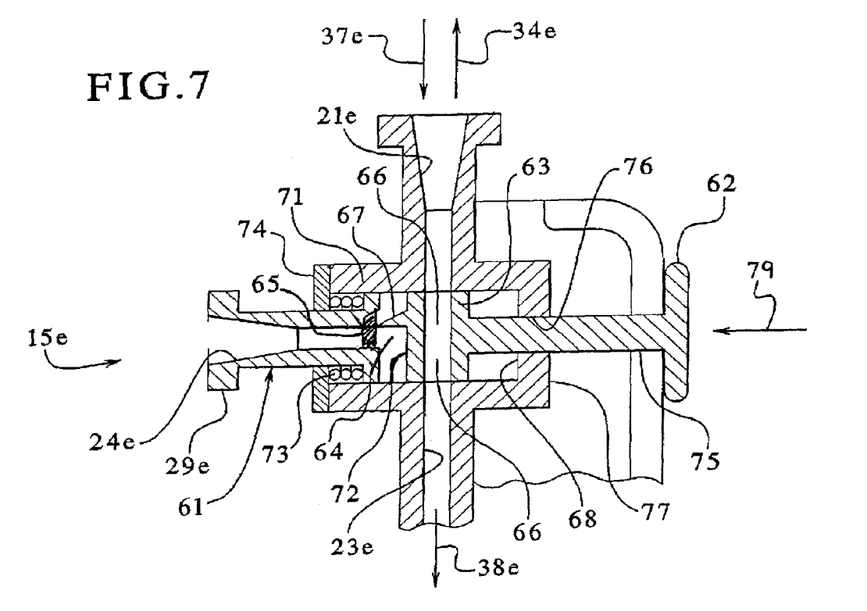
FIG. 7 is another partial sectional view the manifold shown in FIG. 6 but in a second position enabling free flow between the primary injection line and main lumen.
Figure 8A:
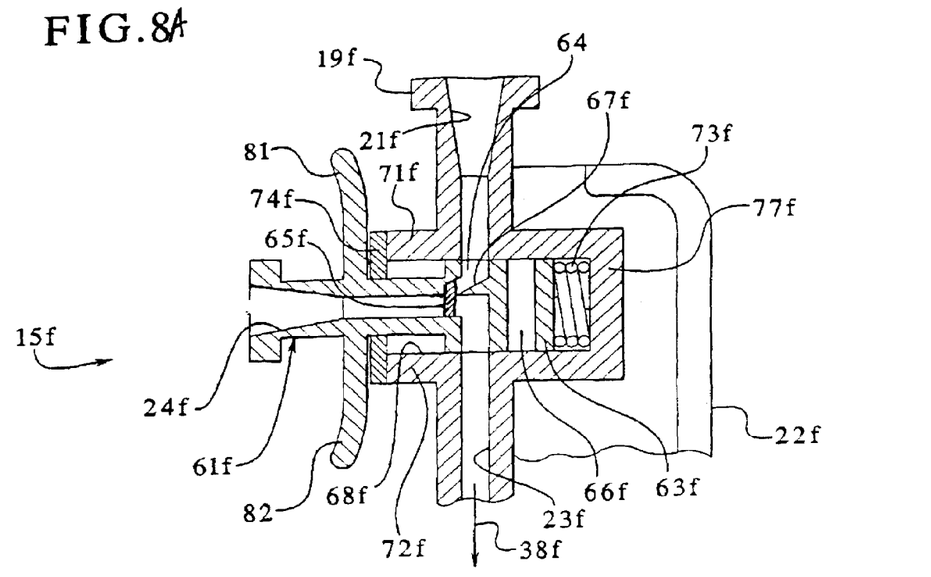
FIG. 8A is a partial sectional view of yet another angiographic fluid manifold made in accordance with the present invention and in a first position and at a rest condition where the syringe, contrast port and primary injection line are isolated.
Figure 8B:
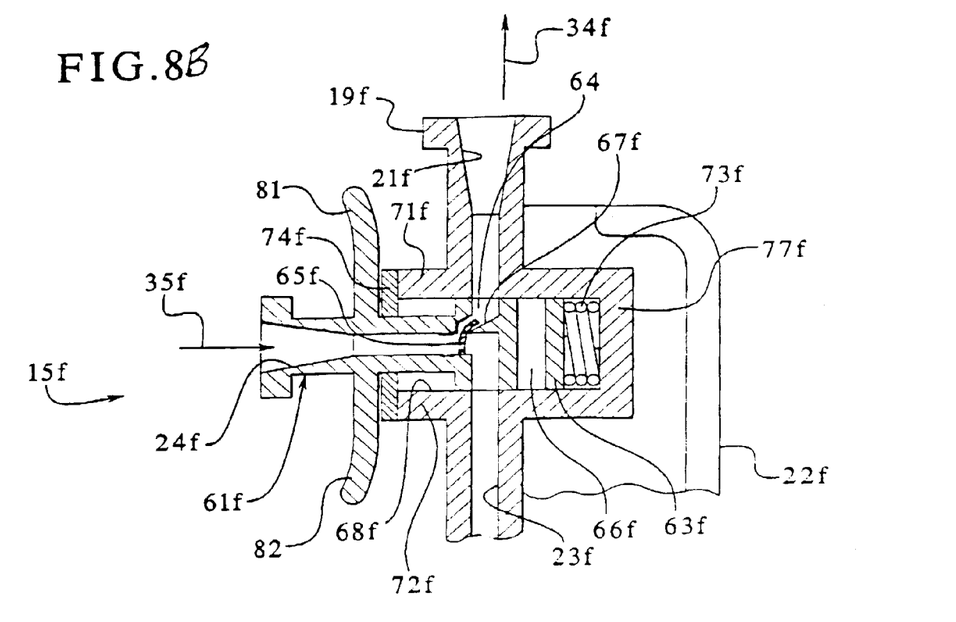
FIG. 8B is another partial sectional view of the angiographic fluid manifold shown in FIG. 8A while still in the first position but with contrast being aspirated from the contrast port towards the syringe.
Figure 8C:
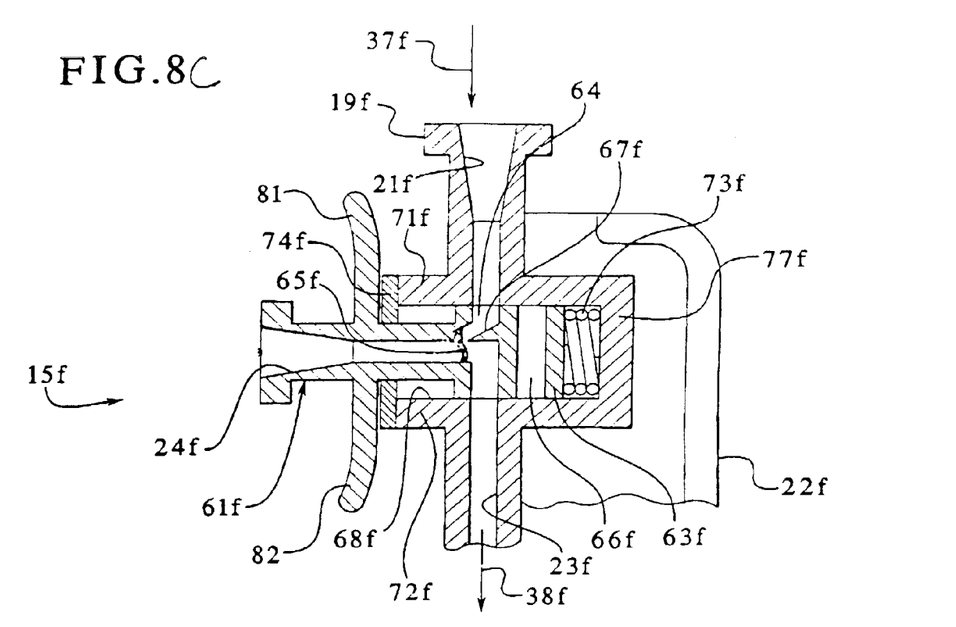
FIG. 8C is another partial sectional view of the angiographic fluid manifold shown in FIGS. 8A and 8B, again in the first position, but with contrast being injected from the syringe towards the primary injection line thereby isolating the contrast port.
Figure 9:
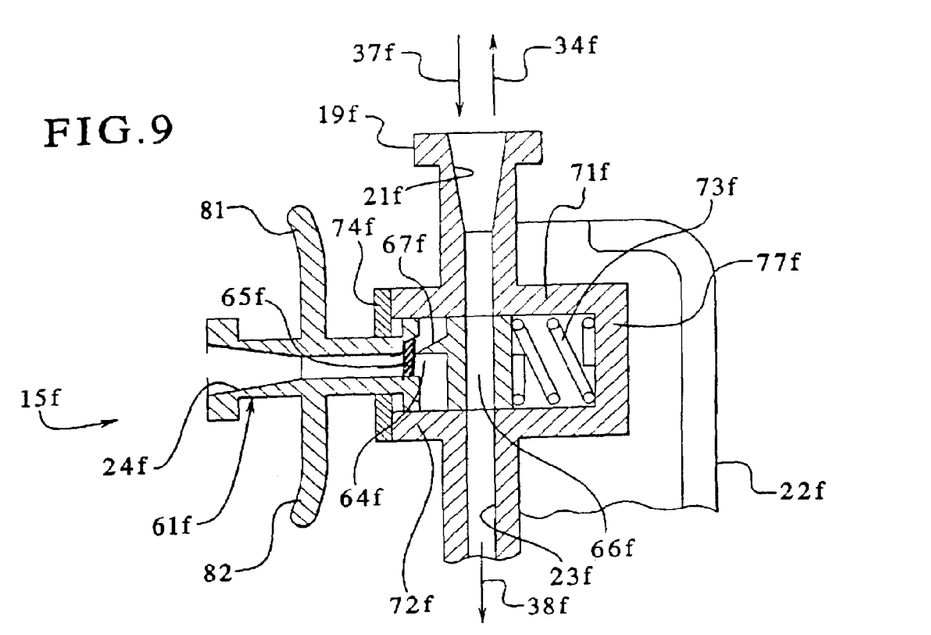
FIG. 9 is another partial sectional view of the angiographic fluid manifold shown in FIG. 8 but in a second position thereby permitting free flow between the primary injection line and main lumen.

Turning to FIGS. 6A-7, certain embodiments of the check valve are explained. For purposes of example, a dual check valve will be explained in greater detail. In FIGS. 6A-6C and 7, the embodiment 15e provides a dual check valve mechanism by way of the sliding actuator or body 61. The body 61 comprises the port 24e, the female connector 29e, a palm pad 62 and a cylindrical wall 63 that defines a first lumen 64 disposed between the wall 63 and the check valve element 65 and a second lumen 66 that is disposed within the cylindrical wall 63. The wall 63 includes a protuberance 67.

The valve element 65 is fixed with respect to the actuator body 61 The actuator body 61 slides within the cavity 68 disposed within the manifold body 22e and into which the main lumen 23e and primary injection line 21e extend. In FIGs 6A-6C, the actuator body 61 is in a first position whereby the first lumen 64 is in-line with the primary injection line 21e and main lumen 23e In the rest position shown in FIG. 6A, the valve element 65 engages the protuberance 67 and the combination of the valve element 65 and protuberance 67 isolates the primary injection line 21e, main lumen 23e and contrast port 24e from one another. As contrast is aspirated in the direction of the arrow 15e, pressure generated in the port 24e biases the valve element 65 towards the right as shown in FIG. 6B and around protuberance 67 to permit fluid flow in the direction of the arrows 15e and 34e (see FIG. 6B). As shown in FIG. 6C, when the contrast is injected from the syringe in the direction of the arrow 37e to the main lumen 23e, the valve element 65 is biased towards the left thereby isolating the secondary injection port 24e and permitting flow in the direction of the arrows 37e and 38e.

Thus, in the first position shown in FIGS. 6A-6C, the secondary injection port 24e, the primary injection port 21e and the main lumen 23e may be isolated (FIG. 6A) or, pressure in the secondary injection port 24e can bias the valve element 65 to the right and around the protuberance 67 to permit flow in the direction of the arrows 35e, 34e as shown in FIG. 6B, or, the valve element 65 may be biased to the left when pressure is generated in the primary injection port 21e by action of the syringe pumping fluid in the direction of the arrows 37e, 38e thereby permitting fluid, such as contrast, to flow from the syringe to the main lumen 23e.

Turning to FIG. 7, the actuator body 61 has been moved to the left relative to the 72 and protuberance 67 thereby placing the second lumen 66 in-line with the main lumen 23e and primary injection line 21e. In this position, flow between the primary injection line 21e and main lumen 23e is provided and the port 24e is isolated from both the primary injection line 21e and main lumen 23e. Specifically, the first-lumen 64 is blocked at both ends by the walls 71, 72 of the cavity 68. A spring 73 may be utilized to bias the actuator body 61 into the position shown in FIGS. 6A-6C. The spring bias may be overcome by applying pressure to the palm pad 62 in the direction of the arrow 74.

The actuator body 61 may be unitary in design or fabricated from multiple components. The portions of the actuator body 61 defining the lumens 64 and 66 may be retained within the cavity 68 along with the spring 73 by way of the retainer plate 74. The palm pad 62 may be threadably connected or otherwise attached to the handle 75 after the handle 75 is extended through the aperture 76 disposed in the wall 77.

In the embodiment 15f shown in FIGS. 8A-8C and 9, instead of a palm pad 62 and handle 75 as shown in FIGS. 6A-6C and 7, finger grips 81, 82 are attached to the actuator body 61f between the port 24f and retainer plate 74f. The spring 73f is trapped between the cylindrical wall 63f of the actuator body 61f and the wall 77. The remaining elements are identical or functionally equivalent to the elements described above in FIGS. 6A-6C and 7.

Figure 10:
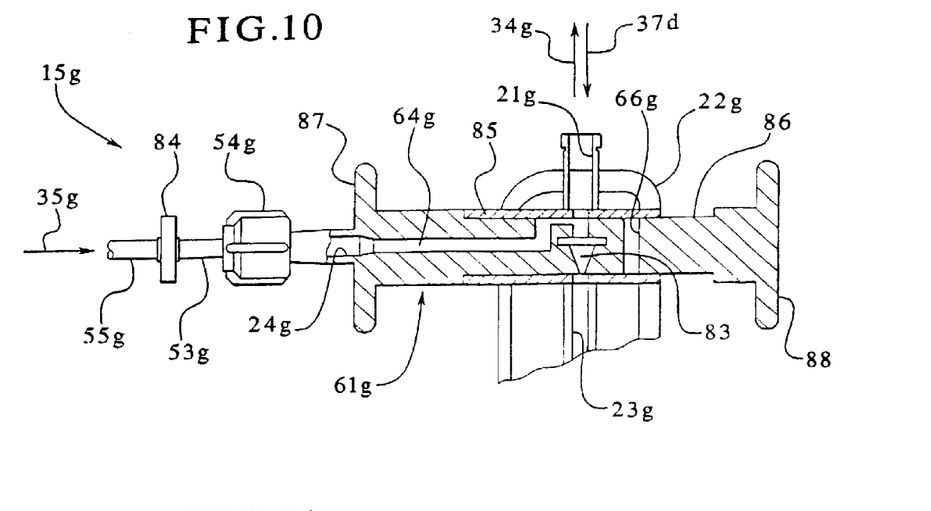
FIG. 10 is a partial schematic sectional view of yet another angiographic fluid manifold made in accordance with the present invention and in a first position thereby permitting fluid flow from the port to the primary injection line.
Figure 11:
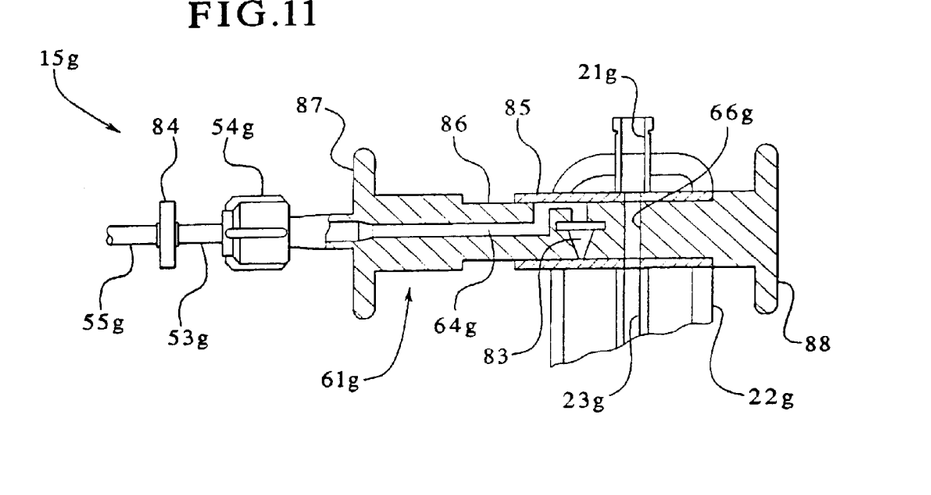
FIG. 11 is another partial schematic sectional view of the angiographic fluid manifold of FIG. 10 but in a second position thereby permitting flow between the primary injection line and main lumen.
Figure 12:
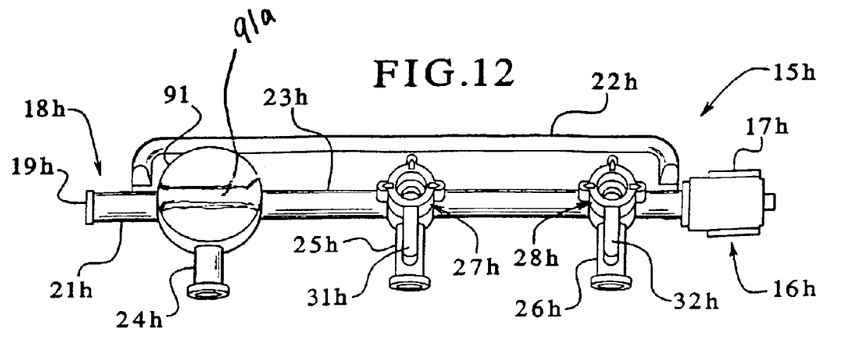
FIG. 12 is a schematic plan view of another angiographic fluid manifold made in accordance with the present invention.

Turning to FIGS. 10 and 11, the embodiment 15g includes a sliding actuator body 61g of a different configuration than the sliding actuator bodies 61 and 61f shown in FIGS. 6-7 and 8-9, respectively Specifically, while the actuator body 61g includes two lumens 64g, 66g like the lumens 64, 66 and 64f, 66f shown in FIGs 6-7 and 8-9, respectively, the lumen 64g includes a one-way check valve 83 that protects the primary injection line 21g and port 24g from back flow from the main lumen 23g. The check valve 83 does not protect the port 24g from back flow from the primary injection line 21g or syringe port Instead, an additional check valve 84 is disposed upstream in the tubing shown at 53g, 55g In the position shown in FIG. 10, fluid may be pumped through the check valve 84 in the direction of the arrow 35g, though the port 24g, though the lumen 64g and into the primary injection line 21g in the direction of the arrow 34g. The one-way check valve 83 prevents any contrast fluid from being pumped or drawn into the primary injection line 21g from the main lumen 23g during the aspiration of the syringe or pump mechanism (not shown) Upon syringe or pump injection, fluid is then pumped in the direction of the arrow 37d, through the one-way check valve 83 and into the main lumen 23g. The check valve 84 prevents any contaminated contrast solution from being injected or pumped into the contrast solution reservoir which is upstream of the tubing 55g. The actuator body 61g is accommodated within a sleeve 85 that is fixed to the manifold body 22g. The sleeve 85 is accommodated in a slot 86 disposed on the outer surface of the actuator body 61g. The actuator body can be slid from the first position shown in FIG. 10 to the second position shown in FIG. 11 by pushing or pulling on either of the handles 87, 88 In the position shown in FIG. 11, the lumen 66g is in-line between the primary injection line 21g and the main lumen 23g thereby providing uninhibited flow between the primary injection line 21g and main lumen 23g.

Figure 13:
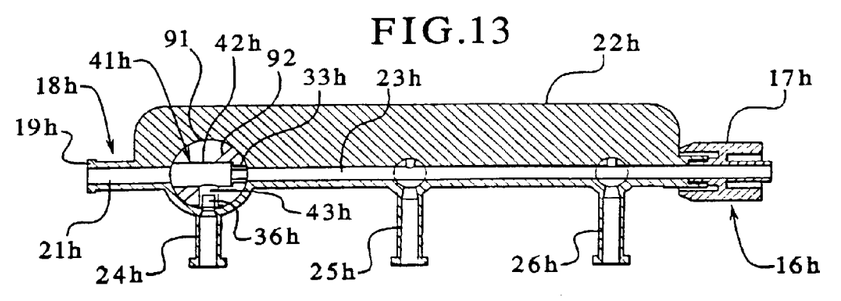
FIG. 13 is a partial sectional view of the angiographic fluid manifold shown in FIG. 12 in a first position permitting flow from the primary injection line to the main lumen and flow from the port to the primary injection line.
Figure 14:
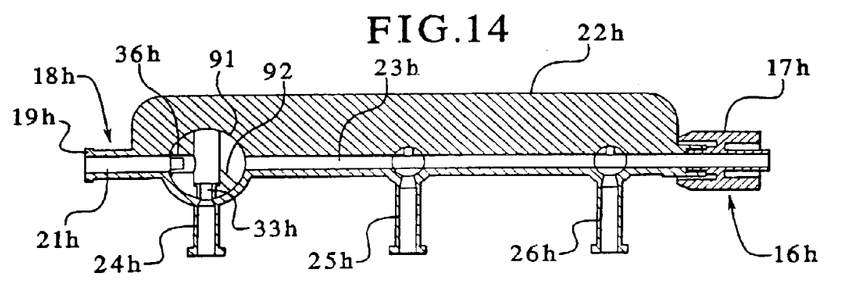
FIG. 14 is another partial sectional view of the angiographic fluid manifold shown in FIG. 12 in a second position thereby permitting flow from the primary injection line to the port.
Figure 15:
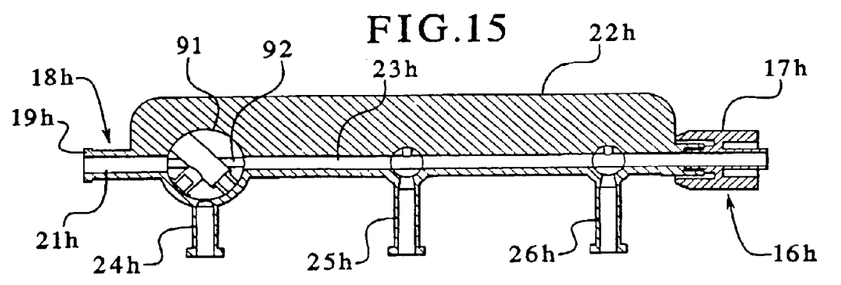
FIG. 15 is another partial sectional view of the angiographic fluid manifold shown in FIG. 12 but in a third position thereby permitting free flow between the primary injection and main lumen.

A further embodiment of a manifold system 15h is illustrated in FIGS. 12-15. In the system 15h, a rotating valve body 91 is disposed at the junction of the primary injection line 21h, port 24h and main lumen 23h. As shown in FIGS. 13-15, the rotating valve body 91 has three positions and movement between these positions can be effectuated by the handle 91a. In FIG. 13, the valve body 91 is a first position whereby the first lumen 42h of the body 41h is in-line between the primary injection line 21h and main lumen 23h. The check valve 33h prevents back flow from the main lumen 23h towards the main injection line 21h. The check valve 36h disposed in the second lumen 43h of the body 41h prevents back flow from the body 41h and the primary injection line 21h to the port 24h. Thus, in the position shown in FIG. 13, fluid may flow from the primary injection 21h to the main lumen 23h and from 24h to 21h.

Turning to FIG. 14, the valve body 91 has been rotated 90° so that the check valve 33h is disposed in-line with the port or contrast line 24h The check valve 36h is disposed in-line with the primary injection line 21h The position shown in FIG. 14 is useful to dump excess contrast solution from the syringe or pump (not shown) back into the port 24h. Thus, excess contrast solution may be pumped from the primary injection line 21h though the check valves 36h, 33h and back into the port 24h to the contrast reservoir (not shown) The position shown in FIG. 14 is useful in the event that no injection has taken place for a period of time during a procedure. Instead of wasting contrast solution which may have been aspirated into the syringe or pump (not shown), the excess solution or solution that is not currently needed may be transferred into the port 24h instead of being wasted.

Turning to FIG. 15, the valve body 91 has been further rotated so that the tertiary lumen 92 is disposed in-line between the primary injection line 21h and main lumen 23h. The position shown in FIG. 15 is useful for aspirating the catheter. Fluid may be drawn through the main lumen 23h in the direction of the primary lumen 21h and aspirated into the syringe or pump and then pumped in the reverse direction toward one of the secondary ports 25h, 26h which can be used as a dump or waste collection.

Thus, an improved angiographic manifold is provided which, in turn, provides check valve protection for both the syringe or saline pump port as well as check valve protection for the contrast fluid reservoir without requiring the physician to manipulate cumbersome stop cock valves. In many of the embodiments, contrast fluid may be drawn into the syringe or pump from the contrast fluid reservoir and injected through the main lumen without manipulating any valve and while providing check valve protection against contamination from fluid disposed in the main lumen.

Although the disclosed devices and methods have been described with reference to preferred embodiments, those skilled in the art will recognize that changes may be made in form and detail with departing from the spirit and scope of this disclosure. As such, it is intended that the foregoing detailed description be regarded as illustrative rather than limiting and it is the following claims, including all equivalents thereof, which are intended to define the scope of the claimed invention.

What is claimed is:

1. A manifold system for use with a syringe, a catheter, and a fluid source, the system comprising:
    a manifold body defining;
    a primary injection line extending through the manifold body from a first end in fluid communication with a junction and a second end adapted for fluid communication with the syringe;
    a main lumen extending through the manifold body from a first end in fluid communication with the junction and a second end adapted for fluid communication with the catheter, wherein the primary injection line and the main lumen are approximately collinear through the manifold body;
    a port extending though the manifold body from a first end in fluid communication with the junction and a second end adapted for fluid communication with the fluid source, wherein the port is disposed approximately perpendicular to the manifold body;
    a valve body disposed in the junction and having a first lumen and a second lumen in fluid communication with the first lumen, the valve body also having a third lumen intersecting the first lumen, wherein the first lumen and the second lumen are connected to form a T-connection;
    a first check valve disposed in an end of the first lumen and oriented to permit fluid flow away from a central portion of the valve body,
    a second check valve disposed in the second lumen and oriented to permit flow toward the central portion of the valve body,
    the valve body being placeable in a first position in which the valve body first lumen extends between the primary injection line first end and the main lumen first end with the first check valve adjacent the main lumen first end, and the valve body second lumen fluidly communicates with the port, thereby to allow fluid flow from the port to the primary injection line while preventing back flow from primary injection line and main lumen to the port, and to allow fluid flow from the primary injection line to the main lumen, while preventing back flow from the main lumen to the primary injection line and port,
    the valve body being further placeable in a second position in which the valve body second lumen fluidly communicates with the primary injection line first end and the valve body first lumen fluidly communicates with the port with the second check valve adjacent the port, thereby to allow fluid flow from the primary injection line to the port while preventing back flow from the port to the primary injection line,
    the valve body being further placeable in a third position in which the valve body third lumen extends between the primary injection line first end and the main lumen first end and in which none of the first, second, or third lumens are in fluid communication with the port.

2. The manifold system of claim 1, in which the third lumen is free of check valves.

3. The manifold system of claim 1 wherein the first lumen and the third lumen are connected at approximately a 45 degree angle.

* * * * *